(12) United States Patent
Kavusi et al.

(10) Patent No.: US 11,875,480 B1
(45) Date of Patent: Jan. 16, 2024

(54) DISTINGUISHING ARTIFACTS FROM PATHOLOGICAL FEATURES IN DIGITAL IMAGES

(71) Applicant: Verily Life Sciences LLC, Mountain View, CA (US)

(72) Inventors: Sam Kavusi, Menlo Park, CA (US); Sunny Virmani, Fremont, CA (US); Eliezer Glik, San Francisco, CA (US); Kira Whitehouse, Palo Alto, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 255 days.

(21) Appl. No.: 17/321,134

(22) Filed: May 14, 2021

Related U.S. Application Data

(60) Provisional application No. 63/025,802, filed on May 15, 2020.

(51) Int. Cl.
| | |
|---|---|
| *G06T 5/00* | (2006.01) |
| *G06T 7/80* | (2017.01) |
| *A61B 3/12* | (2006.01) |
| *A61B 3/14* | (2006.01) |
| *G06T 7/11* | (2017.01) |
| *A61B 3/00* | (2006.01) |
| *G06T 5/50* | (2006.01) |

(52) U.S. Cl.
CPC ............ *G06T 5/002* (2013.01); *A61B 3/0008* (2013.01); *A61B 3/0041* (2013.01); *A61B 3/12* (2013.01); *A61B 3/14* (2013.01); *G06T 5/50* (2013.01); *G06T 7/11* (2017.01); *G06T 7/80* (2017.01); *G06T 2207/10024* (2013.01); *G06T 2207/20081* (2013.01); *G06T 2207/20182* (2013.01); *G06T 2207/30041* (2013.01)

(58) Field of Classification Search
CPC ... G06T 5/002; G06T 5/50; G06T 7/11; G06T 7/80; G06T 2207/10024; G06T 2207/20081; G06T 2207/20182; G06T 2207/30041; A61B 3/0008; A61B 3/0041; A61B 3/12; A61B 3/14
See application file for complete search history.

(56) References Cited

U.S. PATENT DOCUMENTS

| | | | |
|---|---|---|---|
| 10,413,180 B1* | 9/2019 | Barriga | A61B 3/0033 |
| 2012/0063660 A1* | 3/2012 | Imamura | A61B 5/0066 |
| | | | 382/131 |

(Continued)

FOREIGN PATENT DOCUMENTS

| | | |
|---|---|---|
| JP | 2007185417 A | 7/2007 |

*Primary Examiner* — Oneal R Mistry
*Assistant Examiner* — Vaisali Rao Koppolu
(74) *Attorney, Agent, or Firm* — Perkins Coie LLP

(57) ABSTRACT

Introduced here are approaches to assessing whether digital features (or simply "features") detected in digital images by detection models are representative of artifacts that can obscure actual pathologies. A diagnostic platform may characterize each digital feature detected in a digital image based on its likelihood of being an artifact. For instance, a digital feature could be characterized as being representative of an artifact caused by improper illumination, an artifact caused by a physical element that is adhered to the lens through which light is collected by an imaging device, or a pathological feature indicative of a disease.

23 Claims, 10 Drawing Sheets

(56) References Cited

U.S. PATENT DOCUMENTS

| | | | |
|---|---|---|---|
| 2014/0160323 A1* | 6/2014 | Rao | G06T 5/30 |
| | | | 348/242 |
| 2018/0315193 A1* | 11/2018 | Paschalakis | G06V 40/193 |
| 2019/0042828 A1* | 2/2019 | Solanki | A61B 3/12 |
| 2020/0405148 A1* | 12/2020 | Tran | A61B 3/0016 |
| 2022/0358761 A1* | 11/2022 | Ferrante | A61L 2/28 |

* cited by examiner

600

601
Acquire a digital image generated by a retinal camera outside of a diagnostic session

602
Apply a detection model to the digital image to produce an output that identifies digital features in the image that are representative of artifacts

603
Classify each digital feature as being representative of an artifact

604
Generate data for each digital feature identified in the output produced by the detection model

605
Store the data in a structure indicative of a profile associated with the retinal camera

Acquire a series of digital images generated by a retinal camera in rapid succession

802

Apply a detection model to the series of digital images to produce a series of outputs

803

Compare the series of outputs produced by the detection model such that each digital feature is classified as being representative of either an artifact or a pathological feature

804

Generate a notification that specifies whether any digital features have been classified as artifacts

Acquire first pixel data associated with a first digital image of a fundus generated by a retinal camera

902

Acquire second pixel data associated with a second digital image of the fundus generated by the retinal camera

903

Apply a detection model to the first pixel data to identify digital features in the first digital image that are unexpected given a known physiology of the fundus

904

Apply the detection model to the second pixel data to identify digital features in the second digital image that are unexpected given the known physiology of the fundus

905

Classify each digital feature identified in the first and second digital images as being representative of an artifact or a pathological feature

906

Store an indication of digital features, if any, classified as artifacts in a data structure

FIGURE 9

DISTINGUISHING ARTIFACTS FROM PATHOLOGICAL FEATURES IN DIGITAL IMAGES

CROSS-REFERENCE TO RELATED APPLICATIONS

This application claims priority to U.S. Provisional Application No. 63/025,802, titled "Distinguishing Artifacts from Pathological Features in Digital Images" and filed on May 15, 2020, which is incorporated by reference herein in its entirety.

TECHNICAL FIELD

Various embodiments concern computer programs and associated computer-implemented techniques for distinguishing non-pathological features from pathological features in a digital image.

BACKGROUND

Fundus photography involves capturing an image of the fundus to document the retina, which is the neurosensory tissue in the eye that translates optical images into the electrical impulses that can be understood by the brain. The fundus can include the retina, optic disc, macula, fovea, and posterior pole.

Fundus cameras (also referred to as "retinal cameras") are designed to provide an upright, magnified view of the fundus. FIG. 1 depicts an example of a retinal camera. Generally, subjects (also referred to as "patients") will sit at the retinal camera with their chin set within a chin rest and their forehead pressed against a bar. An operator may be responsible for visually aligning the retinal camera and then pressing a shutter release that causes an image of the retina to be generated.

As shown in FIG. 1, light may be focused via a series of lenses through a masked aperture to form an annulus that passes through an objective lens onto the retina. The illuminating light rays are generated by one or more light sources, each of which is electrically coupled to a power source. When the objective lens is aligned with the retina, light reflected by the retina will pass through the un-illuminated hole in the annulus formed by the masked aperture. Normally, alignment is facilitated by having the patient place the eye proximate to a first eyepiece (also referred to as the "patient eyepiece"). Those skilled in the art will recognize that the optics of the retinal camera are generally similar to those of an indirect ophthalmoscope in that the illuminating light rays entering the eye and the imaging light rays exiting the eye follow dissimilar paths.

The imaging light rays exiting the eye may initially be guided toward a second eyepiece (also referred to as the "operator eyepiece") that is used by the operator to assist in aligning/focusing the illuminating light rays. When the operator presses the shutter release, a first mirror can interrupt the path of the illuminating light rays and a second mirror can fall in front of the operator eyepiece, which causes the imaging light rays to be redirected onto a capturing medium. Examples of capturing mediums include film, digital charge-coupled devices (CCDs), and complementary metal-oxide-semiconductors (CMOSs).

Medical professionals, such as optometrists, ophthalmologists, and orthoptists, may use the images generated by a retinal camera to detect and/or monitor diseases. For instance, these images may be used to document indicators of diabetes, age-macular degeneration (AMD), glaucoma, and the like. Accordingly, it is critical that the images are free from artifacts that may influence the analysis performed by these medical professionals.

BRIEF DESCRIPTION OF THE DRAWINGS

This patent or application contains at least one drawing executed in color. Copies of this patent or application publication with color drawings will be provided by the Office upon request and payment of the necessary fee.

FIG. 6 depicts a flow diagram of a process for discovering artifacts outside of a diagnostic session involving a subject.

FIG. 8 depicts a flow diagram of a process for discovering artifacts after digital images are generated as part of a diagnostic session involving a subject.

FIG. 9 depicts a flow diagram of a process for comparing a pair of digital images to discover digital features that are representative of artifacts.

Figure 1:
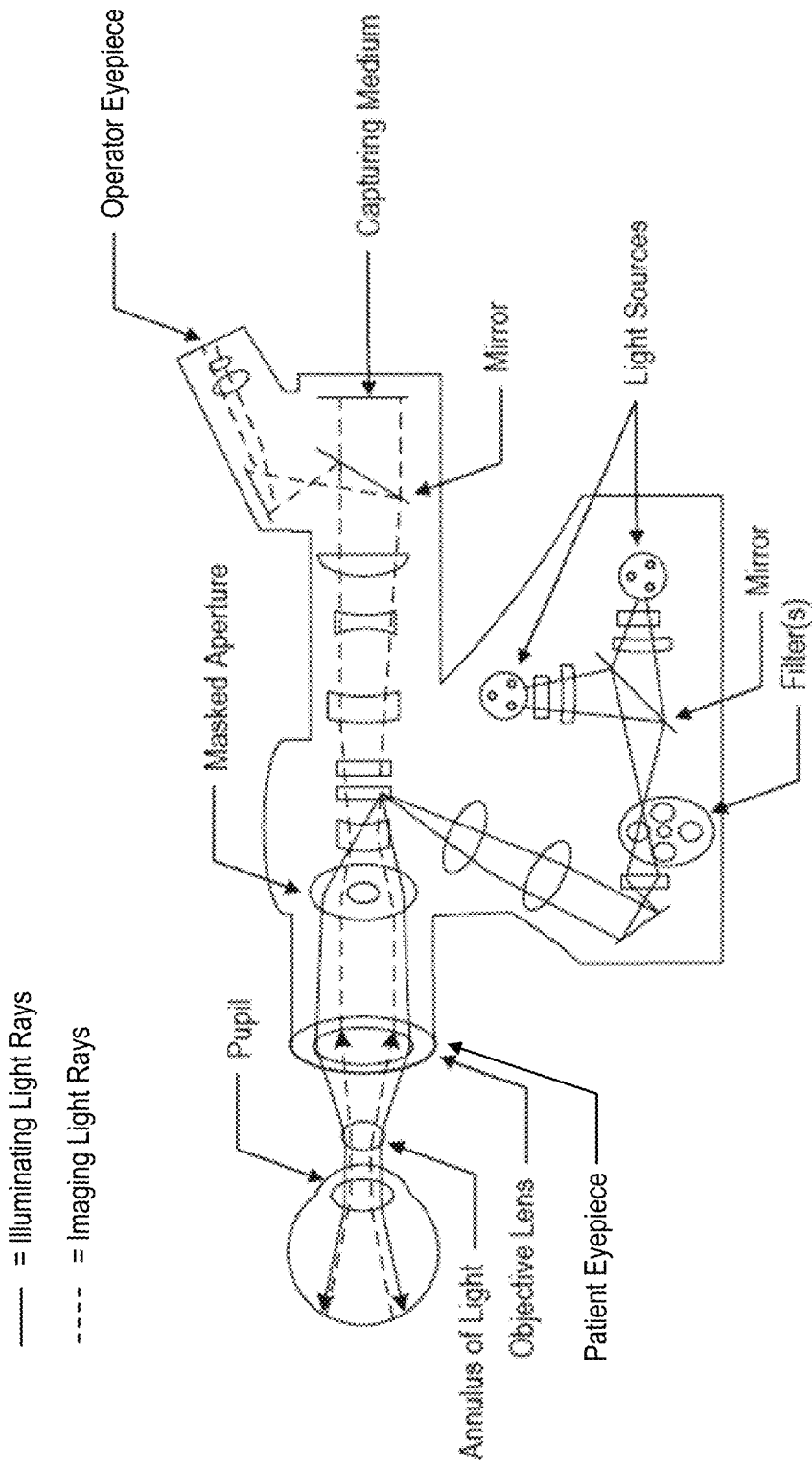
FIG. 1 depicts an example of a retinal camera.

Various features of the technologies described herein will become more apparent to those skilled in the art from a study of the Detailed Description in conjunction with the drawings. Embodiments are illustrated by way of example and not limitation in the drawings, in which like references may indicate similar elements. While the drawings depict various embodiments for the purpose of illustration, those skilled in the art will recognize that alternative embodiments may be employed without departing from the principles of the technologies. Accordingly, while specific embodiments are shown in the drawings, the technology is amenable to various modifications.

DETAILED DESCRIPTION

Figure 2A:
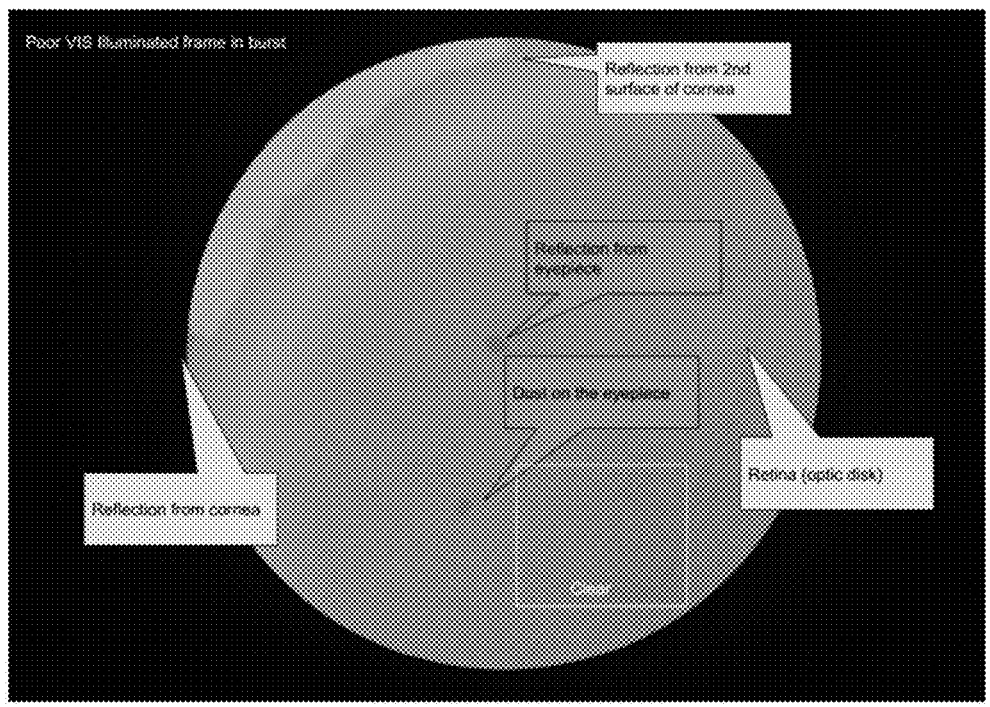
FIGS. 2A-B include examples of digital images that illustrate how artifacts may be visually similar to pathological features.
Figure 2B:
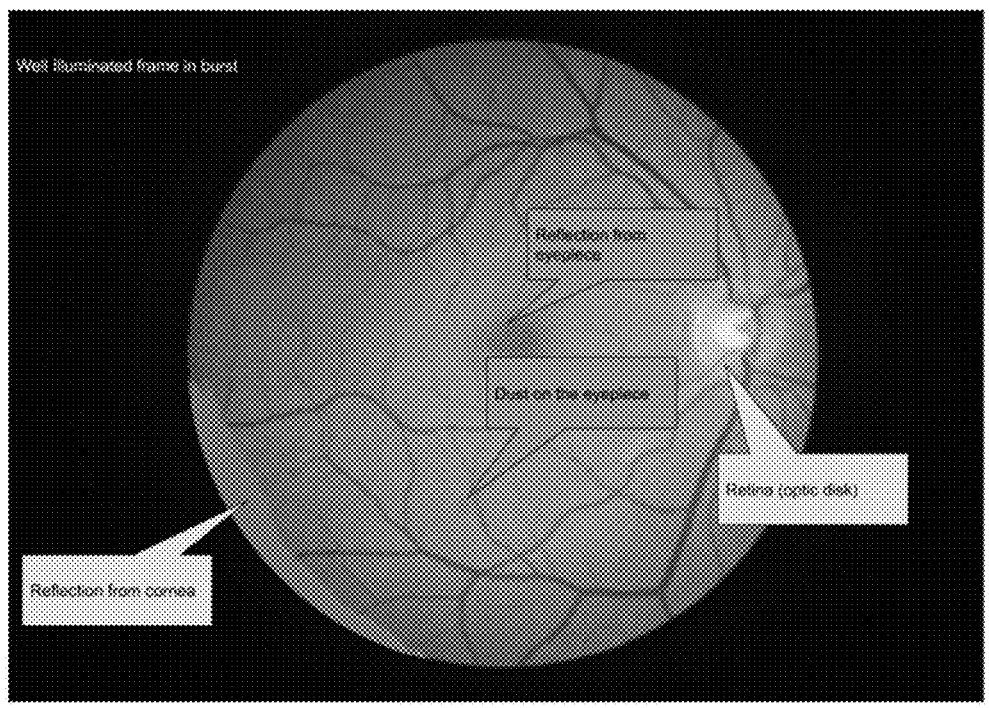

Imaging has historically been an effective means for detecting a variety of ailments. For instance, the digital images generated by retinal cameras are useful for detecting diseases such as diabetic retinopathy and glaucoma. But differentiating the pathological features from the non-pathological features (also referred to as "artifacts") in a digital image can be difficult. FIGS. 2A-B include examples of digital images that illustrate how artifacts may be visually similar to pathological features. FIG. 2A is a poorly illuminated frame captured as part of a burst-capture operation, while FIG. 2B is a properly illuminated frame captured as part of a burst-capture operation. The similarity between these different types of digital features may make it difficult to make proper diagnoses, treatment decisions, etc.

Because differentiating pathological features and artifacts is critical for appropriately screening, diagnosing, and monitoring diseases, it is important that the images generated by retinal cameras be of high quality and fidelity. However, it can be challenging to produce high-quality images for several reasons. First, bright illumination of the retina through the pupil can create optical aberrations that are embodied as artifacts. Examples of such optical aberrations include corneal reflections, iris reflections, and lens flares. Second, physical elements that are adhered to the objective lens (or simply "lens") through which light is collected by the retinal camera may be embodied as artifacts. Examples of physical elements include dust, dirt, oil, grease, hair, and skin. Note that the term "adhered to the lens" is intended to cover physical elements that are adhered, either directly or indirectly, to the lens. Physical elements that are adhered to lens are optically coupled to the light path from the patient eyepiece where the patient locates the eye and the capturing medium of the retinal camera.

Artifacts can obscure the actual pathologies. In some cases, pathological features will be mistaken for artifacts, which may result in under-referral or underdiagnosis of subjects (also referred to as "patients"). In other cases, artifacts will be mistaken for pathological features, which may result in over-referral or overdiagnosis of subjects.

To address the issues caused by bright illumination, some retinal cameras have a very limited eyebox that helps lessen the prevalence and impact of artifacts. For a retinal camera, the eyebox is the three-dimensional (3D) region of space within which the center of a pupil should reside to acquire a digital image of acceptable quality. Normally, the dimensions of the eyebox are defined relative to the patient eyepiece or the operator eyepiece of the retinal camera. While decreasing the size of the eyebox can reduce the severity and/or number of artifacts in a digital image, there are several downsides to this approach. For instance, achieving proper alignment between the eye and the lens of the retinal camera can be difficult when the eyebox is small. As a consequence, operator-subject interactions may be strained during the alignment process due to the difficulty of achieving proper alignment.

To address the issues caused by physical elements, some retinal cameras are designed such that the lens is readily cleanable. However, these cleanings are usually performed on an ad hoc basis. For example, an operator may simply try to remember to clean the lens in the morning before any diagnostic sessions have taken place, in the evening after all diagnostic sessions have taken place, or sporadically throughout the day. Cleanings may be even more inconsistent if a retinal camera is shared by multiple operators. For example, a first operator may assume that a second operator will clean the lens after each diagnostic session, though the second operator may not necessarily do so. This can lead to inconsistency in the artifacts in images generated by the same retinal camera over the course of multiple diagnostic sessions.

Introduced here, therefore, are approaches to assessing whether digital features (or simply "features") detected in digital images by detection models are representative of artifacts that can obscure actual pathologies. As further discussed below, a detection model may be a set of algorithms that are designed and trained to detect digital features in a digital image that are abnormal given an expected output. For example, a detection model may be configured to identify digital features in retinal images that are abnormal given the known physiology of the fundus. This may be accomplished by training the detection model using digital images in which abnormal digital features are labeled. Such an approach enables the detection model to detect abnormal digital features upon being applied to the underlying pixel data of digital images. Generally, each digital feature corresponds to a segmented region of pixels in the digital image to which the detection model was applied.

Abnormal digital features fall into two categories: pathological features and non-pathological features (also referred to as "artifacts"). Since artifacts in digital images can obscure the actual pathology, it is important that those artifacts not be considered when diagnosing, monitoring, or treating subjects. Accordingly, a diagnostic platform may be configured to characterize each digital feature detected in a digital image as either an artifact or a pathological feature. For example, a diagnostic platform may classify each digital feature detected in a digital image as being representative of an artifact or a pathological feature. As further discussed below, the diagnostic platform may simply infer that a given digital feature is representative of a pathological feature upon determining that the given digital feature is not representative of an artifact. In some embodiments, the diagnostic platform may further classify each digital feature determined to be representative of an artifact as either (i) an artifact caused by improper illumination or (ii) an artifact caused by a physical element that is adhered to the lens through which light is collected by the retinal camera.

There are several different approaches to determining whether a digital feature is representative of an artifact. These approaches can be employed independent of one another. Accordingly, while these approaches may be described separately for the purpose of simplification, those skilled in the art will recognize that these approaches (or aspects of each approach) could be performed in combination.

One approach involves discovering artifacts outside of a diagnostic session. Normally, this approach is employed to discover artifacts before a diagnostic session so that an appropriate remediation action (e.g., cleaning or realigning) can be performed; however, this approach could also be employed to discover artifacts after a diagnostic session. Examples of remediation actions include storing information regarding the artifacts, generating a notification that identifies the artifacts, transmitting an instruction to a cleaning system, or performing an image manipulation operation to mitigate an effect of the artifacts. For instance, a diagnostic platform may obtain and/or implement a filter that is designed to remove, mask, or otherwise lessen the impact of artifacts. The diagnostic platform may generate the filter based on the artifacts, or the diagnostic platform may retrieve the filter from a store of filters based on the artifacts. Additionally or alternatively, the diagnostic platform may generate a notification that prompts an operator responsible for managing a retinal camera or a medical professional responsible for reviewing a digital image to indicate whether the filter should be used. Thus, the diagnostic platform may automatically apply the filter to remove artifacts from a digital image, or the diagnostic platform may identify a filter that can be optionally used (e.g., by the operator or medical professional) to remove artifacts from a digital image.

Initially, a diagnostic platform can acquire a digital image generated by a retinal camera outside of a diagnostic session involving a subject. Generally, the digital image does not include the subject who is to be imaged during the diagnostic session. Instead, the digital image may be generated while a cap comprised of an absorptive material is affixed over the lens of the retinal camera. Thereafter, the diagnostic platform can apply a detection model to the digital image and then examine any digital features detected by the detection model. Since no pathological features should be present in the digital image, the diagnostic platform may infer that any digital features are representative of artifacts caused by physical elements being adhered to the lens of the retinal camera.

Another approach involves discovering artifacts during or after a diagnostic session. Initially, a diagnostic platform can acquire a series of digital images generated by a retinal camera in rapid succession (e.g., over the course of several hundred milliseconds as part of a burst-capture operation) and then apply a detection model to the series of digital images. Then, the diagnostic platform may apply a machine learning (ML) algorithm to the digital features detected by the detection model across the series of digital images. By comparing the digital features detected across the series of digital images, the ML algorithm may be able to determine the likelihood that each digital feature is representative of an artifact.

In some embodiments, the diagnostic platform is designed to notify downstream users after discovering that a digital feature representative of an artifact is included in a digital image. The term "downstream user" includes operators responsible for operating retinal cameras during diagnostic sessions, maintainers responsible for maintaining those retinal cameras, and medical professionals responsible for reviewing the digital images generated by those retinal cameras. Accordingly, a diagnostic platform could be configured to notify an operator upon discovering an artifact so that the operator has an opportunity to clean the lens of the retinal camera and then retake digital images that were captured during a diagnostic session. Similarly, a diagnostic platform could be configured to label digital features determined to represent artifacts so that medical professionals ignore those digital features during the review process.

Embodiments may be described with reference to particular types of diseases, imaging devices, artifacts, computer programs, etc. However, those skilled in the art will recognize that these features are similarly applicable to other types of diseases, imaging devices, artifacts, computer programs, etc. For example, embodiments may be described in the context of detection models that are designed to be applied to digital images generated by retinal cameras. However, the relevant features may be similarly applicable to detection models that are designed to be applied to digital images of other parts of the human body. As another example, embodiments may be described in the context of discovering and then classifying artifacts related to physical elements that are adhered to the lens. However, artifacts may also be the result of optical aberrations caused by corneal reflections, iris reflections, lens flares, and the like. However, artifacts could also be digital in nature. For instance, artifacts could be caused by misplacement, misalignment, or improper operation of internal components contained in an imaging device. As an example, the placement of the image sensors and illuminators within an imaging device could cause an artifact in digital images generated by that imaging device. The embodiments described herein are similarly applicable to discovering and classifying these artifacts that are digital in nature.

While embodiments may be described in the context of computer-executable instructions, aspects of the technology can be implemented via hardware, firmware, or software. As an example, a set of algorithms indicative of a detection model designed to detect abnormal digital features that may be representative of artifacts may be executed by a diagnostic platform. The diagnostic platform could be embodied as a software program that offers support for reviewing digital images, rendering diagnoses, and cataloging treatments. In particular, the diagnostic platform may prompt a processor to execute instructions for acquiring a digital image generated by a retinal camera, applying the detection model to the digital image to detect abnormal digital features, classifying each abnormal digital feature as either an artifact or a pathological feature, and then storing data related to those abnormal digital features classified as artifacts in a memory.

Terminology

References in this description to "an embodiment" or "one embodiment" means that the particular feature, function, structure, or characteristic being described is included in at least one embodiment. Occurrences of such phrases do not necessarily refer to the same embodiment, nor are they necessarily referring to alternative embodiments that are mutually exclusive of one another.

Unless the context clearly requires otherwise, the words "comprise" and "comprising" are to be construed in an inclusive sense rather than an exclusive or exhaustive sense (i.e., in the sense of "including but not limited to"). The term "based on" is also to be construed in an inclusive sense rather than an exclusive or exhaustive sense. Thus, unless otherwise noted, the term "based on" is intended to mean "based at least in part on."

The terms "connected," "coupled," or any variant thereof is intended to include any connection or coupling between two or more elements, either direct or indirect. The connection/coupling can be physical, logical, or a combination thereof. For example, objects may be electrically or communicatively coupled to one another despite not sharing a physical connection.

The term "module" refers broadly to software components, firmware components, and/or hardware components. Modules are typically functional components that generate output(s) based on specified input(s). A computer program may include one or more modules. Thus, a computer program may include multiple modules responsible for completing different tasks or a single module responsible for completing all tasks.

When used in reference to a list of multiple items, the word "or" is intended to cover all of the following interpretations: any of the items in the list, all of the items in the list, and any combination of items in the list.

The sequences of steps performed in any of the processes described here are exemplary. However, unless contrary to physical possibility, the steps may be performed in various sequences and combinations. For example, steps could be added to, or removed from, the processes described here. Similarly, steps could be replaced or reordered. Thus, descriptions of any processes are intended to be open-ended.

Overview of Diagnostic Platform

Figure 3:
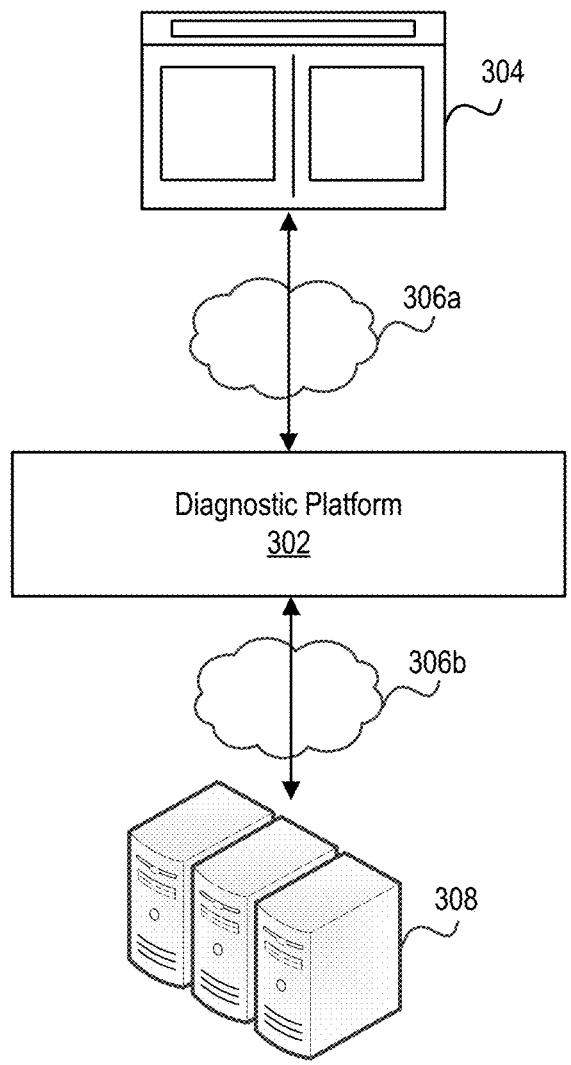
FIG. 3 illustrates a network environment that includes a diagnostic platform.

FIG. 3 illustrates a network environment 300 that includes a diagnostic platform 302. Individuals can interact with the diagnostic platform 302 via an interface 304. For example, medical professionals may access the interface 304 to review the digital images generated by an imaging device, such as a retinal camera, a mobile phone, or a digital camera (e.g., a digital single-lens reflex (DSLR) camera or a mirrorless camera), in order to diagnose the human bodies captured in those images. Moreover, medical professionals may access the interface 304 to review the outputs produced by diagnostic models that have been applied to those images. Diagnostic models may be applied to images generated during a diagnostic session in order to identify the regions of pixels that are clinically or diagnostically relevant. When applied to a digital image, a diagnostic model may produce an output that is indicative of the health state of a corresponding subject. Some diagnostic models produce proposed diagnoses that can be examined by a medical professional, while other diagnostic models produce a visualization component (or simply "visualization") intended to help the medical professional render a diagnosis. The term "health state" can refer to the physical health of the subject with respect to a given disease. For example, a diagnostic platform could be designed to identify digital features that are known to be indicative of diabetic retinopathy (DR), glaucoma, etc.

The decisions made by medical professionals and the outputs produced by diagnostic models will only be appropriate if the analysis is limited to pathological features in the digital images, however, so it is important that the diagnostic platform 302 ensure that non-pathological features (also referred to as "artifacts") are not considered. Identifying the artifacts in digital images, therefore, may be a critical part of the diagnostic process.

To identify the artifacts in a digital image, the diagnostic platform 302 may apply a detection model to the digital image. This digital image could be generated before, during, or after a diagnostic session as further discussed below. When applied to the digital image, the detection model may produce an output that identifies digital features which could be representative of artifacts. Each digital feature may correspond to a segmented region of pixels in the digital image that the detection model has determined is abnormal or unexpected given an expected output. For example, a detection model may be trained to identify digital features in retinal images that are abnormal given the known physiology of the fundus. These abnormal digital features may be representative of either pathological features or artifacts, and therefore may be classified as such. The goal of the detection model may be to determine whether each digital feature is pathological or non-pathological and then ensure that artifacts are not considered (e.g., by diagnostic models or medical professionals) when diagnosing the health state.

As shown in FIG. 3, the diagnostic platform 302 may reside in a network environment 300. Thus, the diagnostic platform 302 may be connected to one or more networks 306a-b. The network(s) 306a-b can include personal area networks (PANs), local area networks (LANs), wide area networks (WANs), metropolitan area networks (MANs), cellular networks, the Internet, etc. Additionally or alternatively, the diagnostic platform 302 can be communicatively coupled to computing device(s) over a short-range wireless connectivity technology, such as Bluetooth® or Near Field Communication (NFC).

The interface 304 is preferably accessible via a web browser, desktop application, mobile application, or over-the-top (OTT) application. Accordingly, the interface 304 may be viewed on a personal computer, tablet computer, mobile workstation, mobile phone, game console, wearable electronic device (e.g., a watch or fitness accessory), network-connected ("smart") electronic device, (e.g., a television or home assistant device), or virtual/augmented reality system (e.g., a head-mounted display).

Some embodiments of the diagnostic platform 302 are hosted locally. That is, the diagnostic platform 302 may reside on the computing device used to access the interface 304. For instance, the diagnostic platform 302 may be embodied as a mobile application executing on a mobile phone or a desktop application executing on a mobile workstation. Other embodiments of the diagnostic platform 302 are executed by a cloud computing service operated by, for example, Amazon Web Services®, Google Cloud Platform™, or Microsoft Azure®. In such embodiments, the diagnostic platform 302 may reside on a network-accessible server system 308 comprised of one or more computer servers. These computer servers can include images generated by imaging devices, subject information (e.g., age, sex, health diagnoses, etc.), imaging device information (e.g., resolution, expected file size, etc.), diagnostic models, detection models, and other assets. Those skilled in the art will recognize that this information could also be distributed amongst a computing device and a network-accessible server system.

While some embodiments are described in the context of network-accessible interfaces, those skilled in the art will recognize that the interfaces need not necessarily be accessible via a network. For example, a computing device may execute a self-contained computer program that does not require network access. Instead, the self-contained computer program may download assets (e.g., images, diagnostic models, detection models, or processing operations) at a single point in time or on a periodic basis.

Figure 4:
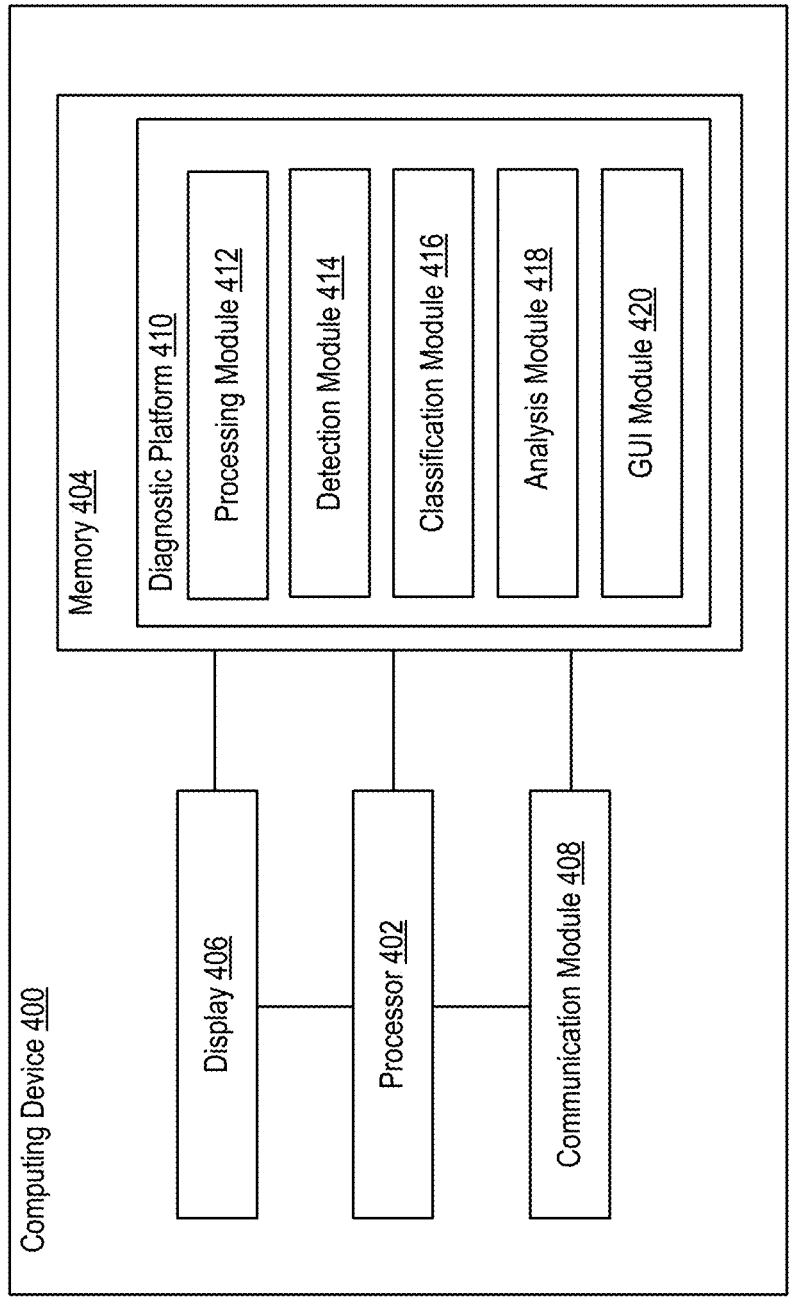
FIG. 4 illustrates an example of a computing device that includes a diagnostic platform able to assess whether a digital feature discovered in a digital image is representative of an artifact.

FIG. 4 illustrates an example of a computing device 400 that includes a diagnostic platform 410 able to assess whether a digital feature discovered in a digital image is representative of an artifact. Such action enables the diagnostic platform 400 to identify the digital features that should not be considered when determining the health state of a subject under examination. For example, if the diagnostic platform 400 discovers that a given digital feature is representative of an artifact, then the diagnostic platform 410 may ensure that the given digital feature is not considered by a diagnostic model applied to the image. As another example, if the diagnostic platform 410 discovers that a given digital feature is representative of an artifact, then the diagnostic platform 410 may label the given digital feature as an artifact so that it is not considered by a medical professional responsible for evaluating the digital image.

The computing device 400 can include a processor 402, a memory 404, a display 406, and a communication module 408. The communication module 408 may be, for example, wireless communication circuitry designed to establish wireless communication channels with other computing devices. Examples of wireless communication circuitry include chips configured for Bluetooth, ZigBee, NFC, and the like. The processor 402 can have generic characteristics similar to general-purpose processors, or the processor 402 may be an application-specific integrated circuit (ASIC) that provides control functions to the computing device 400. As shown in FIG. 4, the processor 402 can be coupled to all components of the computing device 400, either directly or indirectly, for communication purposes.

The memory 404 may be comprised of any suitable type of storage medium, such as a static random-access memory (SRAM), dynamic random-access memory (DRAM), electrically erasable programmable read-only memory (EEPROM), flash memory, or registers. In addition to storing instructions that can be executed by the process 402, the memory 404 can also store data generated by the processor 402 (e.g., when executing the modules of the diagnostic platform 410). Note that the memory 404 is merely an abstract representation of a storage environment. The memory 404 could be comprised of actual memory chips or modules.

The communication module 408 can manage communications between the components of the computing device 400. The communication module 408 can also manage communications with other computing devices. For example, the diagnostic platform 410 may reside on a mobile workstation in the form of a desktop application. In such embodiments, the communication module 408 can communicate with a network-accessible server system responsible for supporting the desktop application and/or an imaging device responsible for generating digital images of subjects. As another example, the diagnostic platform 410 may reside on a computer server of a network-accessible server system. In such embodiments, the communication module 408 can communicate with a computer program executing on a computing device, such as a mobile phone, desktop computer, or mobile workstation. The computing device could be associated with an operator of an imaging device, a maintainer of the imaging device, a medical professional, etc.

For convenience, the diagnostic platform 410 may be referred to as a computer program that resides within the memory 404. However, the diagnostic platform 410 could be comprised of software, firmware, and/or hardware components implemented in, or accessible to, the computing device 400. In accordance with some embodiments described herein, the diagnostic platform 410 may include a processing module 412, a detection module 414, a classification module 416, and an analysis module 418. These modules can be an integral part of the diagnostic platform 410. Alternatively, these modules can be logically separate from the diagnostic platform 410 but operate "alongside" it. Together, these modules may enable the diagnostic platform 410 to identify digital features in digital images that are representative of artifacts.

The processing module 412 may be responsible for applying operations to the pixel data of digital images acquired by the diagnostic platform 410. For example, the processing module 412 may process (e.g., denoise, filter, or otherwise alter) the pixel data so that it is usable by the other modules of the diagnostic platform 410. In some embodiments, the diagnostic platform 410 is configured to acquire raw images generated by an imaging device. In other embodiments, the diagnostic platform 410 is configured to acquire Digital Imaging and Communications in Medicine (DICOM) data objects, each of which includes pixel data corresponding to an image and context data related to attributes of the image. In such embodiments, the processing module 412 may be responsible for extracting the pixel data from each DICOM data object for analysis by the other modules. The context data may include information regarding the subject whose body is captured in the digital image, the imaging device responsible for generating the digital image, or the digital image itself.

After pixel data corresponding to a digital image is acquired, the detection module 414 can identify an appropriate detection model to apply to the pixel data. Generally, the detection model is one of multiple detection models maintained in a library stored in the memory 404. Each detection model may be associated with a different type of imaging device, a different model of imaging device, etc. For instance, a detection model designed to identify artifacts in digital images generated by a first model of retinal camera may differ from a detection model designed to identify artifacts in digital images generated by a second model of retinal camera. Similarly, a detection model designed to identify artifacts in digital images of retinas may differ from a detection model designed to identify artifacts in digital images of skin lesions. The detection model can be comprised of one or more algorithms that, when applied to the pixel data of the image, produce an output that identifies digital features that may be representative of artifacts. At a high level, the output identifies segmented regions of pixels that are abnormal/unusual, and thus candidates for being artifacts.

The classification module 416 may be responsible for determining whether each digital feature identified by the detection model is actually representative of an artifact. As further discussed below, how the classification module 416 accomplishes this may depend on the nature of the digital image. For example, if the digital image is captured outside of a diagnostic session, the classification module 416 may infer that most, if not all, digital features are representative of artifacts since no human body is included in the digital image. As another example, if the digital image is one of a series of digital images captured in rapid succession, the classification module 416 may establish which digital features are representative of artifacts by comparing the digital features detected across the series of digital images. In some embodiments, the classification module 416 may work in concert with the detection module 414 to classify each digital feature. For example, each digital feature may be classified as (i) an artifact caused by improper illumination, (ii) an artifact caused by a physical element that is adhered to the lens through which light is collected by the imaging device, or (iii) a pathological feature indicative of a disease.

The analysis module 418 may be responsible for determining what actions, if any, are appropriate based on the determinations made by the classification module 416. For example, if the classification module 416 determines that a digital feature is representative of an artifact, the analysis module 418 may generate data related to the feature (e.g., its location, classification, etc.) and then store the data in a structure. The structure may be formatted in accordance with a medical image standard. Accordingly, if the pixel data of the image is acquired by the diagnostic platform 410 in the form of a DICOM data object, the analysis module 418 may populate the DICOM data object with data regarding digital features determined to represent artifacts.

Other modules could also be included as part of the diagnostic platform 410. For instance, a graphical user interface (GUI) module 418 may be responsible for generating the interfaces through which individuals can interact with the diagnostic platform 410, view outputs produced by the aforementioned modules, etc. As an example, a visualization that includes information on the digital features determined to represent artifacts may be posted to an interface shown on the display 406 by the GUI module 418.

Figure 5:
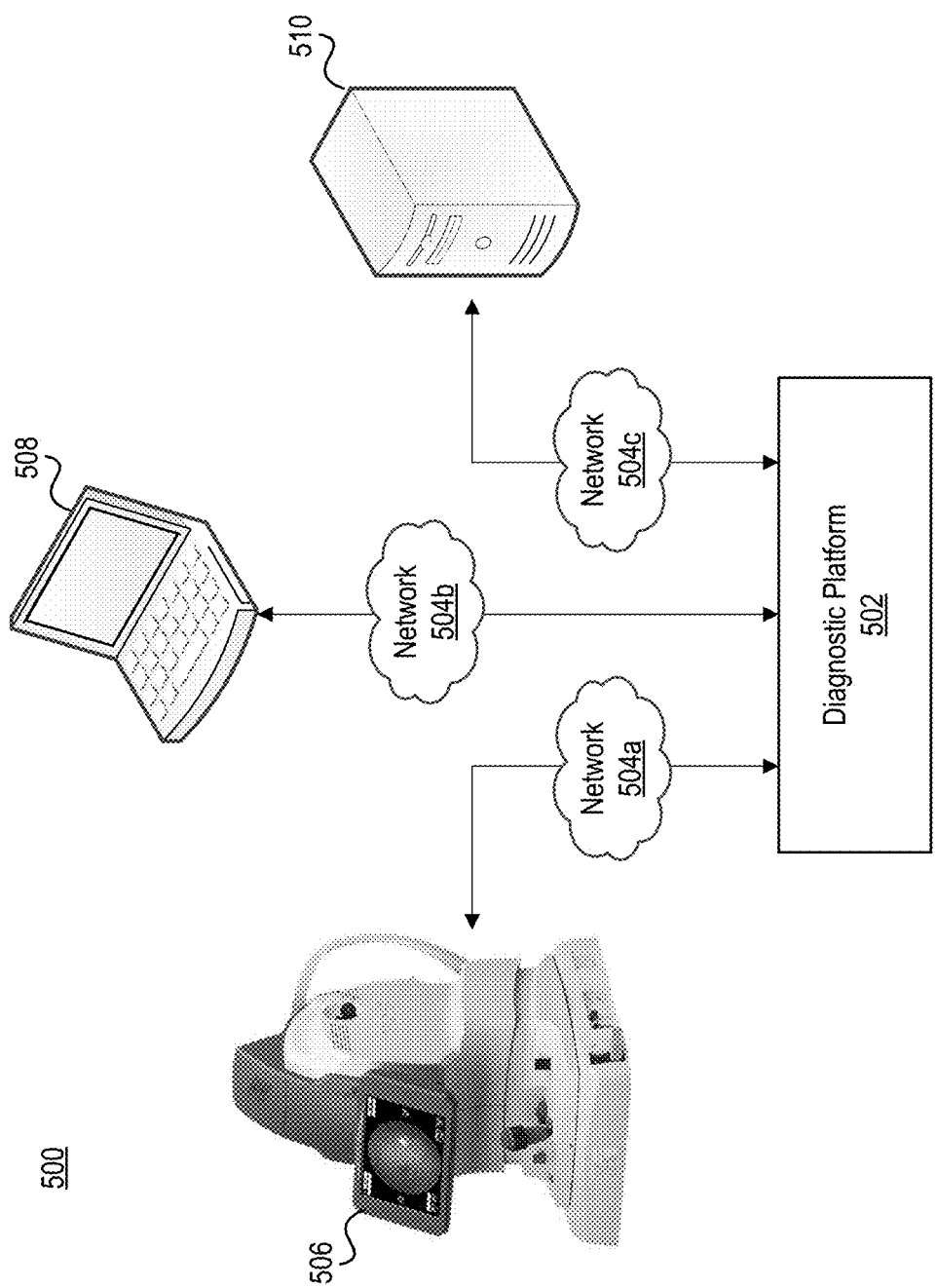
FIG. 5 depicts an example of a communication environment that includes a diagnostic platform configured to acquire data from one or more sources.

FIG. 5 depicts an example of a communication environment 500 that includes a diagnostic platform 502 configured to acquire data from one or more sources. Here, the diagnostic platform 502 may receive data from a retinal camera 506, laptop computer 508, or network-accessible server system 510 (collectively referred to as the "networked devices"). For example, the diagnostic platform 502 may obtain pixel data from the retinal camera 506 and other data (e.g., context data, detection models, processing operations) from the laptop computer 508 or network-accessible server system 510.

The networked devices can be connected to the diagnostic platform 502 via one or more networks 504a-c. The network(s) 504a-c can include PANs, LANs, WANs, MANs, cellular networks, the Internet, etc. Additionally or alternatively, the networked devices may communicate with one another over a short-range wireless connectivity technology, such as Bluetooth or NFC. For example, if the diagnostic platform 502 resides on the network-accessible server system 510, data received from the network-accessible server system 510 need not traverse any networks. However, the network-accessible server system 510 may be connected to the retinal camera 506 and laptop computer 508 via separate Wi-Fi communication channels.

Embodiments of the communication environment 500 may include a subset of the networked devices. For example, some embodiments of the communication environment 500 include a diagnostic platform 502 that receives pixel data from the retinal camera 506 (e.g., in the form of DICOM data objects) and additional data from the network-accessible server system 510 on which it resides. As another example, some embodiments of the communication environment 500 include a diagnostic platform 502 that receives pixel data from a series of retinal cameras located in different environments (e.g., different clinics).

Methodologies for Discovering Artifacts in Images

Introduced here are several approaches to assessing whether the digital features discovered in a digital image by a detection model are representative of artifacts that can obscure actual pathologies. A detection model is a set of algorithm(s) designed and trained to detect digital features in a digital image that may be representative of artifacts. A diagnostic platform may characterize each digital feature based on its likelihood of being an artifact. For instance, the diagnostic platform may be able to characterize each digital feature as either an artifact or a pathological feature. Since pathological features are indicative of a disease, those features should be considered when making decisions while artifacts should not be considered.

As further discussed below, there are several different approaches to confirming whether a digital feature is representative of an artifact or a pathological feature. These approaches can be employed independent of one another. Accordingly, while these approaches are described separately for the purpose of simplification, those skilled in the art will recognize that these approaches (or aspects of each feature) could be performed in combination.

FIG. 6 depicts a flow diagram of a process 600 for discovering artifacts outside of a diagnostic session involving a subject. Initially, a diagnostic platform can acquire a digital image generated by a retinal camera outside of the diagnostic session (step 601). Said another way, the diagnostic platform can acquire a digital image generated by a retinal image during a calibration session that precedes or follows the diagnostic session. Multiple digital images may be generated over the course of the calibration session, and each of these digital images can be analyzed. The calibration session may be representative of an interval of time immediately preceding the diagnostic session or an interval of time immediately following the diagnostic session. Alternatively, the digital image may be generated during an initiation process (e.g., that is performed upon being powered on).

Since the digital image is generated outside of the diagnostic session, the digital image does not include the patient who is to be imaged during the diagnostic session. Instead, the digital image may be generated based on light reflected by the ambient environment through the lens of the retinal camera. In some embodiments, the retinal camera generates the digital image using light that is emitted through its lens toward a cap that is affixed over the lens. The inner surface of the cap may be comprised of an absorptive material. Since the absorptive material is designed to absorb light emitted through the lens, the diagnostic platform may infer that any digital features in the digital image are likely to represent artifacts.

In some embodiments the digital image is generated in conjunction with visible radiation (also referred to as "visible light") emitted by the retinal camera, while in other embodiments the image is generated in conjunction with infrared radiation (also referred to as "infrared light") emitted by the retinal camera. Infrared light is electromagnetic radiation with wavelengths longer than those of visible light. Wavelengths in the infrared spectrum range normally range from the nominal red edge of the visible spectrum at 700 nanometers (nm) to approximately 1 millimeter (mm).

Figure 7:
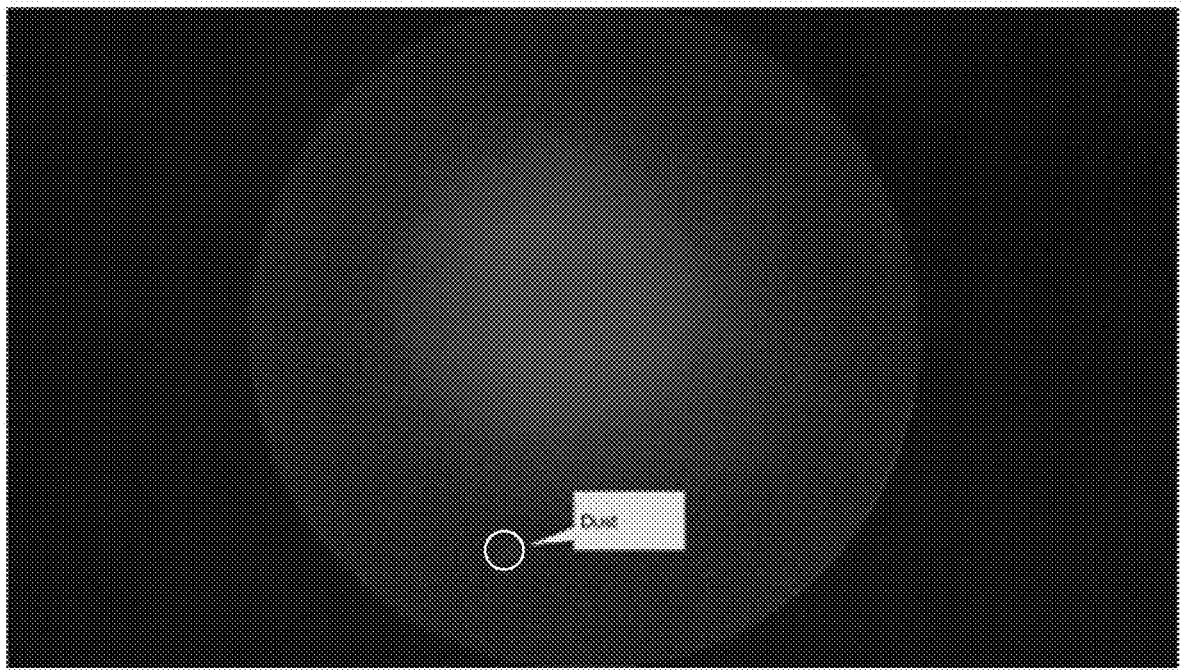
FIG. 7 includes a retinal image captured under infrared light in which a digital feature representative of an artifact (here, caused by dust) has been identified by a detection model.

Then, the diagnostic platform can apply a detection model to the digital image to produce an output that identifies digital features in the digital image that are representative of artifacts (step 602). Each digital feature may correspond to a segmented region of pixels in the digital image that are determined to be abnormal or unusual. As an example, FIG. 7 includes a retinal image captured under infrared light in which a digital feature representative of an artifact (here, caused by dust) has been identified by a detection model.

The diagnostic platform can then classify each digital feature as being representative of an artifact (step 603). For example, the diagnostic platform may classify each digital feature based on whether the corresponding segmented region of pixels is representative of (i) an artifact caused by improper illumination or (ii) an artifact caused by a physical element that is adhered to the objective lens through which light is collected by the retinal camera. This determination may be based on characteristics of the corresponding segmented region of pixels, such as its size, location, shape, color, etc. For instance, some artifacts may change in shape depending on the size and/or shape of the optical stop of the retinal camera. Much like a DSLR camera, the size and/or shape of the optical stop could be adjusted (e.g., from a first diameter to a second diameter, or from a circular aperture to a star aperture as a consequence of the diameter adjustment). In such a scenario, adjusting the size and/or shape of the optical stop over a series of digital images that are captured in rapid succession may provide clues as to whether each segmented region of pixels is actually representative of an artifact.

Moreover, this determination may be based on a comparison of the appearance of the corresponding segmented region of pixels in a frame captured in conjunction with infrared light and a frame captured in conjunction with visible light. In some embodiments, this determination is based on how the corresponding segmented region of pixels varies as different light sources (e.g., light-emitting diodes) are illuminated. Some artifacts will noticeably vary when different light sources are illuminated.

In some embodiments, the diagnostic platform performs or facilitates a dynamic illumination operation to determine whether a digital feature is representative of an artifact. Assume, for example, that a retinal camera includes multiple light sources that can be separately illuminated. For instance, the retinal camera may include a series of light-emitting diodes that can be sequentially illuminated to emit light at different angles. Since physical elements that cause artifacts, such as dust and mucus, will look different when illuminated at different angles, the diagnostic platform may be able to determine the likelihood that a digital artifact is an artifact based on the series of digital images captured in conjunction with light emitted by the series of light-emitting diodes. Additional information on dynamic illumination can be found in US Publication No. 2019/0046031, titled "Dynamic Illumination During Retinal Burst Imaging," and US Publication No. 2020/0015676, titled "Retinal Camera with Light Baffle and Dynamic Illuminator for Expanding Eyebox," each of which is incorporated herein by reference in its entirety. At a high level, dynamic illumination may employ pupil tracking (or some other approach) to establish characteristics of the pupil (e.g., its size and three-dimensional location) and then drive light sources that are spatially separated to allow for an eyebox of allowable locations where the retinal camera could obtain a good retinal image.

The diagnostic platform may generate data for each digital feature identified in the output produced by the detection model (step 604). For each digital feature, this data could specify a location (e.g., in terms of pixel coordinates) and/or a classification of the corresponding segmented region of pixels. In some embodiments, this data is stored in a structure indicative of a profile associated with the retinal camera (step 605). Such an approach allows the diagnostic platform to readily generate notifications identifying the artifacts whenever digital images generated by the retinal camera are under review. In other embodiments, this data is stored in a structure formatted in accordance with a medical image standard. For example, this data may be populated into DICOM data objects corresponding to digital images generated by the retinal camera over the course of a diagnostic session.

The diagnostic platform may raise these artifacts to the attention of downstream users. For example, the diagnostic platform may notify an operator responsible for operating the retinal camera that the lens should be cleaned. As another example, the diagnostic platform may notify a maintainer responsible for maintaining the retinal camera that servicing is necessary. As another example, the diagnostic platform may notify a medical professional responsible for reviewing digital images generated during a diagnostic session so that the artifact does not influence pathological decisions.

Additionally or alternatively, the diagnostic platform may automatically perform some action in an attempt to address the artifacts. For example, if the diagnostic platform determines that at least one digital feature is representative of an artifact caused by a physical element that is adhered to the lens through which light is collected by the retinal camera, the diagnostic platform may transmit an instruction a cleaning system configured to clean the lens of the retinal camera responsive to receiving the instruction.

FIG. 8 depicts a flow diagram of a process 800 for discovering artifacts after digital images are generated as part of a diagnostic session involving a subject. Initially, a diagnostic platform can acquire a series of digital images generated by a retinal camera in rapid succession (step 801). For example, the series of digital images may be generated by the retinal camera over the course of several hundred milliseconds as part of a burst-capture operation. Normally, each digital image in the series of digital images includes the fundus (or at least a portion thereof) of the subject undergoing examination during the diagnostic session.

Then, the diagnostic platform can apply a detection model to the series of digital images to produce a series of outputs (step 802). Each output in the series of outputs may correspond to a digital image in the series of digital images, and each output may identify digital features in the corresponding digital image that may be representative of an artifact. Normally, each digital feature corresponds to a segmented region of pixels that is unexpected given the known physiology of the fundus.

However, as discussed above, these segmented regions of pixels could be representative of artifacts or pathological features. Accordingly, the diagnostic platform may compare the series of outputs produced by the detection model such that each digital feature is classified as being representative of an artifact or a pathological feature (step 803). For example, the diagnostic platform may establish the degree of consistency between segmented regions of pixels across the series of digital images. The degree of consistency can be established in several different ways.

In some embodiments, for each segmented region of pixels, the diagnostic platform defines a positional relationship with respect to a known physiological structure (e.g., the optic disc, macula, or posterior pole) and then determines a count of digital images that include a segmented region of pixels with a similar positional relationship to the known physiological structure. The degree of consistency may be based on the count of digital images. In such embodiments, a higher degree of consistency may correspond to a lower likelihood that a given segmented region of pixels is representative of an artifact since artifacts are unlikely to move as the fundus shifts.

In other embodiments, for each segmented region of pixels, the diagnostic platform defines a positional relationship with respect to a pixel boundary (e.g., using the pixel coordinates) and then determines a count of digital images that include a segmented region of pixels with a similar positional relationship to the pixel boundary. Again, the degree of consistency may be based on the count of digital images. In such embodiments, a higher degree of consistency may correspond to a higher likelihood that a given segmented region of pixels is representative of an artifact since artifacts are unlikely to move as the fundus shifts.

Additionally or alternatively, the diagnostic platform may apply an ML model to the segmented regions of pixels that is trained to identify artifacts based on differences in color, shadow, contrast, and the like between similarly positioned segmented regions of pixels across the series of digital images. Based on these characteristics, the ML model may be able to distinguish between artifacts that are consistent with varying illumination and physiological features that are consistent with varying illumination.

Thereafter, the diagnostic platform can generate a notification that specifies whether any digital features have been classified as artifacts (step 804). The notification may include a visualization in which each segmented region of pixels that has been classified as being representative of an artifact is visually highlighted. For example, these segmented regions could be outlined, labeled, etc.

FIG. 9 depicts a flow diagram of a process 900 for comparing a pair of digital images to discover digital features that are representative of artifacts. At a high level, the process 900 pertains to an approach in which a retinal camera generates light to illuminate artifacts that reflect some of the light back into the retinal camera. Such an approach allows artifacts to be more easily isolated. As discussed above with respect to FIG. 6, artifacts may be readily identifiable if no retinal signal is present in the digital image(s) under consideration. For instance, a cap whose inner surface is comprised of an absorptive material may be affixed over the lens of the retinal camera to ensure that no retinal signal is present. In such a situation, any digital features discovered in digital image(s) generated by the retinal image while the cap is affixed over lens may be inferred to represent artifacts.

Initially, a diagnostic platform can acquire first pixel data associated with a first digital image of a fundus generated by a retinal camera (step 901) and second pixel data associated with a second digital image of the fundus generated by the retinal camera (step 902). The first and second digital images may be generated by the retinal camera before, during, or after a diagnostic session involving a subject. For example, the first and second digital images could be generated in rapid succession (e.g., over a span of several hundred milliseconds) during the diagnostic session. As another example, the first digital image could be generated at the beginning of the diagnostic session while the second digital image could be generated at the end of the diagnostic session.

The diagnostic platform can apply a detection model to the first pixel data to identify digital features in the first digital image that are unexpected given the known physiology of the fundus (step 903). Similarly, the diagnostic platform can apply the diagnostic model to the second pixel data to identify digital features in the second digital image that are unexpected given the known physiology of the fundus (step 904). As discussed above, the diagnostic platform can then classify each digital feature identified in the first and second digital images as being representative of an artifact or a pathological feature (step 905).

The diagnostic platform may store an indication of digital features, if any, classified as artifacts in a data structure (step 906). As an example, for each digital feature classified as an artifact, the diagnostic platform may store information regarding its location, classification, etc. The data structure may be indicative of a profile that is associated with the retinal camera.

Unless contrary to physical possibility, it is envisioned that the steps described above may be performed in various sequences and combinations. For example, the dynamic illumination operation described above with respect to FIG. 6 could be employed in the context of FIG. 8 or 9. Thus, the first and second digital images generated by the retinal camera may be captured in conjunction with light emitted by different light sources. Such an approach may enable the diagnostic platform to establish whether the digital features are different when illuminated from different angles. As another example, the diagnostic platform may cause digital images to be displayed on an interface while the processes described herein are being performed. Such action may be performed contemporaneous with alerting an operator that an artifact may exist in these digital images (e.g., through the surfacing of a notification). Such an approach allows the operator to determine whether additional digital images should be generated (e.g., after cleaning the lens). Alternatively, the processes described herein may be performed after a diagnostic session has been completed. While this approach prevents digital images from being retaken by the operator, any digital features that are representative of artifacts could still be labeled so that those segmented regions of pixels are not considered when the digital images are subsequently reviewed.

Other steps may also be included in some embodiments. For example, the diagnostic platform may acquire digital images taking during past diagnostic sessions involving a given subject. By comparing digital features detected in a current diagnostic session against digital features detected in those past diagnostic sessions, the diagnostic platform may have a better understanding of which segmented regions of pixels are abnormal or unexpected. For instance, the diagnostic platform may infer that a given digital feature is more likely representative of a pathological feature if a similar digital feature was discovered in another digital image of the same subject that was generated in the preceding weeks or months. Likewise, the diagnostic platform may infer that a given digital feature is more likely representative of an artifact is a similar digital feature was not discovered in another digital image of the same subject that was generated in the preceding weeks or months.

Processing System

Figure 10:
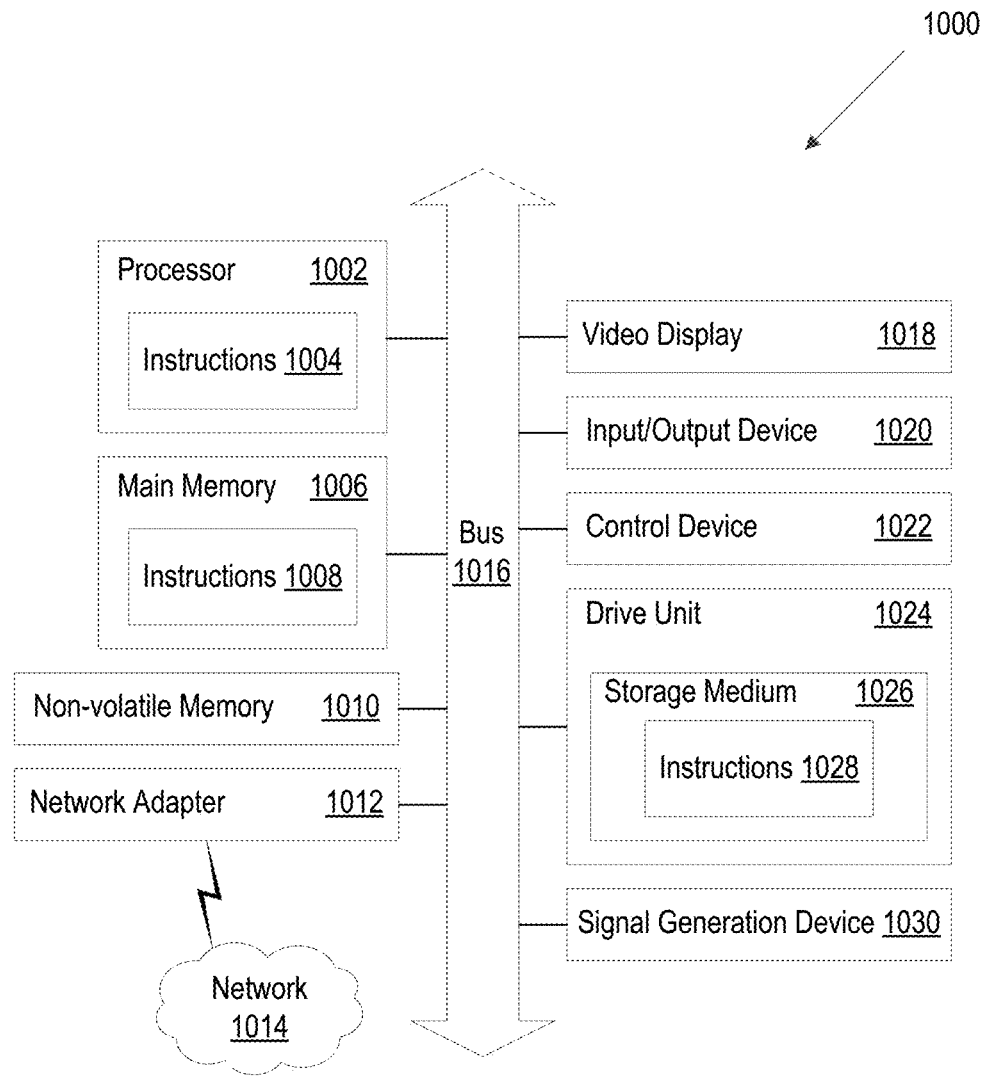
FIG. 10 is a block diagram illustrating an example of a processing system in which at least some operations described herein can be implemented.

FIG. 10 is a block diagram illustrating an example of a processing system 1000 in which at least some operations described herein can be implemented. For example, some components of the processing system 1000 may be hosted on a computing device that includes a diagnostic platform (e.g., diagnostic platform 302 of FIG. 3 or diagnostic platform 410 of FIG. 4).

The processing system 1000 may include one or more central processing units ("processors") 1002, main memory 1006, non-volatile memory 1010, network adapter 1012 (e.g., network interface), video display 1018, input/output devices 1020, control device 1022 (e.g., keyboard and pointing devices), drive unit 1024 including a storage medium 1026, and signal generation device 1030 that are communicatively connected to a bus 1016. The bus 1016 is illustrated as an abstraction that represents one or more physical buses and/or point-to-point connections that are connected by appropriate bridges, adapters, or controllers. The bus 1016, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), Inter-Integrated Circuit ($I^2C$) bus, or an Institute of Electrical and Electronics Engineers (IEEE) standard 1394 bus (also referred to as "Firewire").

The processing system 1000 may share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), virtual/augmented reality systems (e.g., a head-mounted display), or another electronic device capable of executing a set of instructions (sequential or otherwise) that specify action(s) to be taken by the processing system 1000.

While the main memory 1006, non-volatile memory 1010, and storage medium 1026 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 1028. The term "machine-readable medium" and "storage medium" shall also be taken to include any medium that is capable of storing, encoding, or carrying a set of instructions for execution by the processing system 1000.

In general, the routines executed to implement the embodiments of the disclosure may be implemented as part of an operating system or a specific application, component, program, object, module, or sequence of instructions (collectively referred to as "computer programs"). The computer programs typically comprise one or more instructions (e.g., instructions 1004, 1008, 1028) set at various times in various memory and storage devices in a computing device. When read and executed by the one or more processors 1002, the instruction(s) cause the processing system 1000 to perform operations to execute elements involving the various aspects of the disclosure.

Moreover, while embodiments have been described in the context of fully functioning computing devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 1010, floppy and other removable disks, hard disk drives, optical disks (e.g., Compact Disk Read-Only Memory (CD-ROMS), Digital Versatile Disks (DVDs)), and transmission-type media such as digital and analog communication links.

The network adapter 1012 enables the processing system 1000 to mediate data in a network 1014 with an entity that is external to the processing system 1000 through any communication protocol supported by the processing system 1000 and the external entity. The network adapter 1012 can include a network adaptor card, a wireless network interface card, a router, an access point, a wireless router, a switch, a multilayer switch, a protocol converter, a gateway, a bridge, bridge router, a hub, a digital media receiver, and/or a repeater.

The network adapter 1012 may include a firewall that governs and/or manages permission to access/proxy data in a computer network and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall may additionally manage and/or have access to an access control list that details permissions including the access and operation rights of an object by an individual, a machine, and/or an application, and the circumstances under which the permission rights stand.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

Remarks

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes certain embodiments and the best mode contemplated, the technology can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the technology with which that terminology is associated. In general, the terms used in the following claims should not be construed to limit the technology to the specific embodiments disclosed in the specification, unless those terms are explicitly defined herein. Accordingly, the actual scope of the technology encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the technology be limited not by this Detailed Description, but rather by any claims that issue on an application based hereon. Accordingly, the disclosure of various embodiments is intended to be illustrative, but not limiting, of the scope of the technology as set forth in the following claims.

What is claimed is:

1. A method comprising:
   acquiring, by a processor, a digital image generated by a retinal camera during a calibration session that occurs outside of a diagnostic session involving a patient,
      wherein the digital image does not include the patient who is to be imaged during the diagnostic session, and therefore is based on light reflected by an ambient environment through a lens of the retinal camera;
   applying, by the processor, a machine learning model to the digital image to produce an output that identifies a digital feature in the digital image that is representative of an artifact with no pathological value,
      wherein the digital feature corresponds to a segmented region of pixels in the digital image;
   classifying, by the processor, the segmented region of pixels corresponding to the digital feature as being representative of (i) an artifact that is caused by an optical aberration or (ii) an artifact that is caused by a physical element adhered to the lens of the retinal camera; and
   performing, by the processor, a remediation action based on an outcome of said classifying.

2. The method of claim 1, wherein the digital image is generated by the retinal camera in conjunction with infrared radiation emitted by the retinal camera.

3. The method of claim 1, wherein the digital image is one of a series of digital images generated by the retinal camera in conjunction with light emitted by a series of light sources, and wherein each digital image in the series of digital images is generated in conjunction with light emitted by a corresponding light source of the series of light sources.

4. The method of claim 1, further comprising:
   storing, by the processor, data regarding the digital feature in a structure formatted in accordance with a medical image standard,
      wherein the data specifies a location and a classification of the segmented region of pixels.

5. The method of claim 1, wherein said performing the remediation action comprises:
   causing display of a notification that identifies the segmented region of contiguous pixels determined to represent an artifact.

6. The method of claim 5, wherein said performing the remediation action comprises:
   enabling an individual to identify a filter to be applied to the digital image so as to remove the artifact.

7. The method of claim 5, wherein the notification is posted to
an interface that is accessible to a medical professional responsible for analyzing digital images generated during the diagnostic session, or
an interface that is accessible to an operator responsible for operating the retinal camera during the diagnostic session.

8. The method of claim 1, further comprising:
determining, by the processor, that the digital feature is representative of an artifact caused by a physical element that is adhered to a lens through which light is collected by the retinal camera; and
wherein said performing the remediation action comprises:
transmitting an instruction to a cleaning system that cleans the lens of the retinal camera responsive to receiving the instruction.

9. The method of claim 1, wherein the digital feature is one of multiple digital features identified in the digital image by the machine learning model.

10. A non-transitory computer-readable medium with instructions stored thereon that, when executed by a processor, cause the processor to perform operations comprising:
acquiring a series of digital images generated by a retinal camera in rapid succession;
applying a detection model to the series of digital images to produce a series of outputs,
wherein each output in the series of outputs corresponds to a digital image in the series of digital images, and
wherein each output identifies digital features in the corresponding digital image that may be representative of artifacts;
comparing the series of outputs produced by the detection model such that each digital feature is classified as being representative of either an artifact or a pathological feature; and
generating a notification that specifies whether any digital features have been classified as being representative of artifacts, wherein
the notification includes
an instruction to clean a lens of the retinal camera to remove a physical element adhered to the lens of the retinal camera, or
an instruction to employ a filter to mitigate an effect of an optical aberration from the image.

11. The non-transitory computer-readable medium of claim 10, wherein each digital feature corresponds to a segmented region of contiguous pixels.

12. The non-transitory computer-readable medium of claim 11, wherein said comparing comprises:
estimating a degree of consistency between segmented regions of pixels across different digital images.

13. The non-transitory computer-readable medium of claim 12, wherein said estimating is performed by a machine learning model that considers differences in color, shadow, or contrast between the segmented regions of pixels.

14. The non-transitory computer-readable medium of claim 12, wherein said estimating comprises:
for each segmented region of pixels,
defining a positional arrangement with respect to a known physiological feature, and
determining a count of digital images in the series of digital images that include a segmented region of pixels with a similar positional arrangement with respect to the known physiological feature.

15. The non-transitory computer-readable medium of claim 14, wherein the degree of consistency is based on the count of digital images, and wherein a higher degree of consistency corresponds to a lower likelihood that a given segmented region of pixels is representative of an artifact.

16. The non-transitory computer-readable medium of claim 14, wherein the degree of consistency is based on the count of digital images, and wherein a higher degree of consistency corresponds to a higher likelihood that a given segmented region of pixels is representative of an artifact.

17. The non-transitory computer-readable medium of claim 11, wherein said comparing comprises:
for each segmented region of pixels,
defining a positional arrangement with respect to a pixel boundary, and
determining a count of digital images in the series of digital images that include a segmented region of pixels with a similar positional arrangement with respect to the pixel boundary.

18. The non-transitory computer-readable medium of claim 10, wherein the notification includes a visualization component in which each segmented region of pixels that has been classified as being representative of an artifact is visually highlighted.

19. The non-transitory computer-readable medium of claim 10, wherein the notification is viewable on a display of the retinal camera.

20. A computer-implemented method comprising:
acquiring first pixel data associated with a first digital image of a fundus generated by a retinal camera;
acquiring second pixel data associated with a second digital image of the fundus generated by the retinal camera;
applying a detection model to the first pixel data to identify a first digital feature in the first digital image that is unexpected given a known physiology of the fundus,
wherein the detection model is trained on images labeled as being representative of different types of artifacts, the different types of artifacts including artifacts caused by optical aberrations and artifacts caused by physical elements;
applying the detection model to the second pixel data to identify a second digital feature in the second digital image that is unexpected given the known physiology of the fundus;
classifying the first and second digital features identified in the first and second digital images as being representative of either physiological features or artifacts;
determining, based on said classifying, that a digital feature was classified as an artifact, the digital feature being the first digital feature or the second digital feature; and
storing an indication of the digital feature in a data structure.

21. The computer-implemented method of claim 20, wherein the data structure is indicative of a profile that is associated with the retinal camera.

22. The computer-implemented method of claim 20, wherein the first and second digital images are generated by the retinal camera during a diagnostic session in which the fundus is imaged.

23. The computer-implemented method of claim 20, further comprising:
determining, based on said classifying, that another digital feature was classified as an artifact, the other digital feature being whichever of the first and second digital features is not the digital feature; and storing an indication of the other digital feature in another data structure.

* * * * *